United States Patent
Kaffka et al.

[11] Patent Number: 5,970,424
[45] Date of Patent: *Oct. 19, 1999

[54] METHOD AND APPARATUS FOR QUALIFYING AN OBJECT

[76] Inventors: Károly Kaffka, Ábel Jenő, H-1113 Budapest; János Jákó, Oltvány u. 34, H-1112 Budapest; Gyula Domján, Gyöngyház u. 2, H-1132 Budapest; István Vályi-Nagy, Lovas út 6/b, H-1012 Budapest; László Gyarmati, Nádasdy Kálmán u. 37, H-1046 Budapest; László Gödölle, Király u. 70, H-1068 Budapest, all of Hungary

[*] Notice: This patent issued on a continued prosecution application filed under 37 CFR 1.53(d), and is subject to the twenty year patent term provisions of 35 U.S.C. 154(a)(2).

[21] Appl. No.: 08/945,526
[22] PCT Filed: Apr. 29, 1996
[86] PCT No.: PCT/HU96/00024
    § 371 Date: Oct. 28, 1997
    § 102(e) Date: Oct. 28, 1997
[87] PCT Pub. No.: WO96/34272
    PCT Pub. Date: Oct. 31, 1996

[30] Foreign Application Priority Data

Apr. 28, 1995 [HU] Hungary .................... 9501215
Apr. 28, 1995 [HU] Hungary .................... 9501216

[51] Int. Cl.$^6$ .................................................. G01N 21/35
[52] U.S. Cl. ................................. 702/30; 702/28
[58] Field of Search .................... 364/498, 725.01, 364/726.01, 726.02, 726.03, 731, 734; 382/100; 250/339.01; 702/22–25, 27, 28, 30

[56] References Cited

U.S. PATENT DOCUMENTS

| | | |
|---|---|---|
| 4,783,754 | 11/1988 | Bauck et al. . |
| 4,963,745 | 10/1990 | Maggard . |
| 5,349,188 | 9/1994 | Maggard .................... 250/343 |
| 5,360,972 | 11/1994 | DiFoggio et al. .................... 364/498 |
| 5,397,899 | 3/1995 | DiFoggio et al. .................... 364/498 |
| 5,596,196 | 1/1997 | Cooper et al. .................... 356/301 |

FOREIGN PATENT DOCUMENTS 0 584 931  3/1994  European Pat. Off. .

OTHER PUBLICATIONS

Kaffka et al., Qualitative Analysis By Near Infrared Spectroscopy Central Food Research Institute pp. 135–144, Jun. 1990.

Calculus, Larson and Hostetler $2^{nd}$ ed. Larson et al. Pub. D.C. Heath and Co. Lexington, Mass Dec. 1982.

Proceeding Third International Conference on Near Infrared Spectroscopy, Brussels, BE, Jun. 25–29 1990, pp. 135–144, XP000577940 cited in the application K.J. Kaffka et al: "Qualitative (comparative) analysis by near infrared spectroscopy".

Analytical Chemistry, vol. 64, No. 6, Mar. 15, 1992, Columbus US, pp. 664–667, XP000577237, P. Robert et al, "Identification of chemical constituents by multivariate near-infrared spectral imaging" cited in the application.

(List continued on next page.)

*Primary Examiner*—John Barlow
*Assistant Examiner*—Craig Steven Miller
*Attorney, Agent, or Firm*—Oblon, Spivak McClelland, Maier & Neustadt, P.C.

[57] ABSTRACT

A method and apparatus for qualifying an object. Several characteristic values of the object are determined and arranged in a sequence in a polar coordinate system having an origin. At least one quality point is determined as the center of gravity on the basis of the positions of the characteristic values in the polar coordinate system. The object is qualified according to the position of the quality point in the polar coordinate system. In determining the quality point, the characteristic values are taken into account by weighting with their distances from the origin of the polar coordinate system.

25 Claims, 8 Drawing Sheets

OTHER PUBLICATIONS

Proceedings Second International NIRS Conference, Tsukuba, JP, 1989, pp. 393–404, XP000577996 cited in the application S.K. Taylor: NIR imaging spectroscopy: measuring the distribution of chemical components.

Proceedings of the International Diffuse Spectroscopy Conferences, Aug. 1992, Qualitative Analysis Applying NIR Spectroscopy, Karoly J. Kaffka, Central Food Research Institute, Budapest, Hungary.

The Proceedings of the $2^{nd}$ International NIRS Conference NIR Expert System for Sample Identification, Karoly J. Kaffka and Laszlo S. Gyarmati Central Food Research Institute, H–1111 Budapest, Budafoki ut 59, Hungary.

METHOD AND APPARATUS FOR QUALIFYING AN OBJECT

BACKGROUND OF THE INVENTION

1. Field of the Invention

The invention is a method and apparatus for qualifying an object.

2. Discussion of the Background

By plotting alterations of a physical characteristic measurable on a material as a function of another physical characteristic a spectrum is obtained. A spectrum is obtained for example, when an optical characteristic (transmission or reflection) of a material is plotted as a function of the wavelength of the illuminating radiation. Spectra are useful information sources relating to qualities, e.g. composition, of a material examined. However, the relationship between data representing qualities of the examined material and a certain spectrum of the sample cannot be described today in most cases in the form of mathematical equations. Therefore, determining relationships in an empirical way is relied upon. For this, a large number of samples with known qualities are required and spectra of all samples must be measured. In present day measurement technology it is not rare that a single spectrum is represented by a thousand spectrum values. The processing of the spectrum means that operations are to be carried out with these one thousand data.

Obtaining and interpreting useful information require in most cases the application of complicated methods of mathematical statistics. Even the majority of such spectrum recording and evaluating instruments and methods become suitable for determining qualities of samples of unknown composition from their spectra after a "learning" process of a large number of measurements (calibration) carried out on a series of samples of known qualities. Of methods of mathematical statistics applied for processing spectra, a relatively simple and widely applied method is the MLR (Multiple Linear Regression) method. Good results can be achieved by the MLR method, however, it has the disadvantage that only spectrum values associated with some discrete values of independent variable are used in determining the quality or qualities sought, although other spectrum values also carry valuable information. Further, when the program is run on a PC configuration, the calculation period may be rather long.

Shortening of the calculation period and the learning process may be achieved by transforming spectra into Fourier domain and taking into consideration the first 20 to 50 members of the Fourier series, only. This method represents a substantial data reduction, generally by one order of magnitude, in a way that in determining the reduced data all original spectrum data play a role. A spectral pattern classification system using discrete Fourier transformation is described in U.S. Pat. No. 4,783,754. The signal to be classified is sampled and the samples are multiplied by weighting constants inherent in the system prior to performing discrete Fourier transformation. The preprocessing ensures that data blocks from similar sources will have spectra that are close to one another in the Fourier domain.

A method different from those above, implementing a large-scale data reduction based on geometry, has also been suggested by K. J. Kaffka and L. S. Gyarmati in an article entitled Qualitative (Comparative) Analysis by Near Infrared Spectroscopy, Proceedings of the Third International Conference on Near Infrared Spectroscopy, Jun. 25–29, 1990, Brussels, Belgium, pp. 135–144. According to the method, spectrum values measured are not plotted in a usual rectangular coordinate system, but in a polar coordinate system, hypothetical masses of equal amount are assigned to the spectrum points so obtained, and their center of mass, that is the center of gravity is determined. The polar coordinate system was called "quality plane", the center of gravity was named "quality point" and the vector drawn from the origin of the coordinate system to the quality point was called "quality vector". According to this method, the quality, e.g. composition, of materials that can be characterised by their spectra can be described by the quality point or quality vector, respectively.

In many cases, however, the examined object is not homogeneous, and the distribution of various components is not uniform in the object. At the same time, knowledge about planar (spatial) distribution of the components could be important e.g. from the aspect of quality. To this end, elaboration of such a special technique is required, which enables measurement of reflection spectra of objects in two dimensions. The size of the object could vary between wide limits. The inhomogeneous surface could be of one $cm^2$ or smaller size, e.g. when examining pharmaceuticals, cosmetics or foodstuff, it could be of some $dm^2$ size, e.g. when protein or fat distribution of a body part is to be determined for medical purposes, but it could also be of several thousand $km^2$ size, e.g. when grain crops of a country are to be predicted on the basis of aerial photographs taken at different wavelengths about the arable land. The solution is to project the surface of the object to be examined to a photosensitive matrix.

According to the publication of S. K. Taylor and W. F. McClure: NIR Imaging Spectroscopy: Measuring the Distribution of Chemical Components, Proceedings of the 2nd International NIRS Conference, Tsukuba, Japan, 1989, pp. 393–404, a photosensitive camera including a charge coupled device (CCD) as an image detector was used to distinguish healthy and dead tissue parts of tree leaves, with 320*240 detector elements (pixels) which could distinguish 256 light intensity levels. On one wavelength this represents 76,800 eight-bit data. In order to obtain reliable physical-chemical information from the intensity data measured on the pixels, the measurement should be carried out on several hundred wavelengths. The large quantity of data resulting would exceed the data processing possibilities of a normal PC. Even in the method mentioned above, measurement was carried out on six wavelengths by changeable filters installed in a rotating disk.

In the publication of P. Robert, D. Bertrand, M. F. Devaux and A. Sire: Identification of Chemical Constituents by Multivariate Near-Infrared Spectral Imaging, Analytical Chemistry, Vol. 64, No. 6, Mar. 15, 1992, pp. 664–667, measurements carried out on grain by a NIR video camera with 512*512 pixels, on 21 wavelength values are described. The pixels could distinguish 256 light intensity stages. In order to reduce the noise eight pictures were averaged and in order to facilitate data processing signals of four neighbouring pixels were averaged.

SUMMARY OF THE INVENTION

It is an objective of the present invention to provide a further development of the qualification method based on the quality plane discussed above.

It is a further objective of the invention to provide a method and an apparatus suitable for analysing two-dimensional pictures of objects, while making sure that very large quantity of spectral image data could be handled by normal data processing capacity of PCs.

Another objective of the invention is to provide a qualifying method which is less sensitive to noise.

In the course of examining and practically testing the quality plane method, we have come to the following insights. We have found that in polar coordinate system, in the case of equal masses assigned to the spectrum points, the effect of spectrum values closer to the origin is relatively high because they are crowded in the vicinity of the origin and so they play a substantial role in determining the center of gravity. However, the absorption peaks characteristic of the composition of a product are generally located far from the origin of the polar coordinate system, while wider absorption valleys hardly characterising the composition are located close to the origin. This means that irrelevant spectrum values are highlighted. We have recognised that for qualification a more advantageous quality point can be determined if not hypothetical masses of equal amount, but those with masses corresponding to the distance from the origin are assigned to the spectrum points. The position of the center of gravity, that is the quality point so defined, is more influenced by peak spectrum values characteristic for the product to be qualified.

Thus, on the one hand, the invention is a method for qualifying an object comprising the steps of determining several characteristic values of the object, arranging the characteristic values in a sequence in a polar coordinate system having an origin, determining at least one quality point as center of gravity on the basis of positions of the characteristic values in the polar coordinate system and qualifying the object according to position of the at least one quality point in the polar coordinate system. According to the invention, the at least one quality point is determined as center of gravity of hypothetical masses assigned to the positions of the characteristic values in such a way that amounts of said masses correspond to the characteristic values to which they are assigned.

By means of the method of the invention it can be achieved that high value features especially characterising the examined object, e.g. absorption peaks of a spectrum, play a bigger role in defining the quality point or quality points. Thus, the quality point or quality points according to the invention is/are better to characterise the object than the quality point obtained by the known method.

According to the invention, the assignment of hypothetical masses can be carried out in various ways. The relation between the amounts of masses and the respective characteristic values may preferably be linear or quadratical. For example, said hypothetical masses assigned to the positions of the characteristic values are points located at the positions of the characteristic values, wherein the amounts of masses of said points correspond to the characteristic values to which they are assigned linearly or quadratically.

Determination of the at least one quality point can be carried out in a way that said hypothetical masses assigned to the positions of the characteristic values are straight lines connecting consecutive positions of the characteristic values, wherein the amounts of masses of said lines correspond to their lengths. This method corresponds to a linear weighting with the distance from the origin. The role of important characteristic values can be further increased so that said hypothetical masses assigned to the positions of the characteristic values are surface portions confined by straight lines connecting consecutive positions of the characteristic values and the origin, wherein the amounts of masses of said surface portions correspond to their areas. This method corresponds to a quadratic weighting with the distance from the origin.

The method according to the invention enables several types of object qualification, which are described in the following specification and in the set of claims.

The method according to the invention is not only suitable for qualifying objects but also for determining some of their qualities. To this end, according to the invention, lines associated with predetermined values of at least one quality of the object are established in the polar coordinate system, and value or values of the at least one quality are determined on the basis of the position of the quality point or any of the quality points in relation to these lines.

The value of a quality of the object may also be determined from coordinate values of the quality point according to a linear equation, wherein constants of the equation are obtained by regression calculation.

The method according to the invention can be applied to any characteristics of any examined object under the condition that the values of the characteristics should be suitable for being expressed in numbers. The characteristics could be, for example, values of a spectrum. It is possible, however, that the characteristics are quantities of different dimensions. In a practical application of the method according to the invention, the characteristic values must always be arranged into a sequence in an identical way and the one or more quality points are to be determined in the polar coordinate system on the basis of the characteristic values arranged in a sequence in the predetermined way.

Another aspect of the present invention relates to a method for qualifying an object in two dimensions comprising the steps of determining several characteristic values of the object as a function of a parameter for each image point of a two-dimensional picture of the object and qualifying the object on the basis of the characteristic values determined for the image points. According to the invention the method is characterised by arranging the characteristic values for each image point in a sequence in a polar coordinate system having an origin, determining a quality point as center of gravity on the basis of positions of the characteristic values in the polar coordinate system for each image point in such a way that, after determination of each characteristic value, components of coordinates of the quality point for each image point are calculated, these components are added to sums of the components calculated previously and the coordinates of the quality point are defined as values proportional to the sums obtained after the determination of the last characteristic value, and by qualifying the object according to the position of the quality point determined in the polar coordinate system for each image point.

By means of this method it is possible to qualify two-dimensional objects with a great number of image points and a great number of characteristic values with substantially less data processing capacity than by known methods.

The method according to the invention enables different types of qualification of a two-dimensional object. Advantageously, it can be carried out in a way that a single quality point is determined for each image point, and the qualification of the object is performed on the basis of an average quality point determined by averaging the coordinates of the quality points for all image points. This may be carried out by taking into account the positions of the quality points in relation to the average quality point. For example, a statistical parameter of distances between the quality points and the average quality point may be determined, or it can be examined whether the distances of quality points are within a predetermined distance from the average quality point. By means of such homogeneity investigations, the uniform quality of a product can be controlled in industrial applications.

The invention is also suitable for determining a quality of the object in two dimensions. On the basis of the quality point obtained for each image point, values of an object quality intended to be examined can be preferably determined for all image points. On this basis, a picture of a two-dimensional distribution of the quality can be generated, or it can be examined whether the values of the quality are within a predetermined range of values. It is also possible to determine an average value of the quality and, on the basis of the values of the quality determined for the image points, the object is qualified according to whether the values of the quality are within a predetermined range in relation to the average value.

The object's quality to be examined may be determined for each image point in a way that lines associated with predetermined values of the quality are determined in the polar coordinate system, and the value of the quality is determined on the basis of the position of the quality point in relation to these lines.

The value of the quality of the object for each image point may also be determined from the coordinate values of the quality point by a linear equation, where constants of the equation are obtained by regression calculation.

The method according to the invention can be applied well in the case when the characteristic of the examined object is the intensity of a radiation as a function of wavelength. In this case the intensity values are arranged in a sequence according to the wavelength values, i.e. the value range of the wavelength is made to correspond to the angular range of the polar coordinate system, thereby defining one or more quality points in the polar coordinate system. In some cases it could be advantageous if the value range of the wavelength is made to correspond to two or more angular ranges, and a quality point is determined for each angular range, and the qualification of the object for each image point or the determination of a quality of the object is carried out on the basis of the two or more quality points.

On the other hand, the invention is an apparatus for qualifying an object comprising a device for determining several characteristic values of the object and a data processing unit for arranging the characteristic values determined in a sequence in a polar coordinate system having an origin, said data processing unit comprising means for determining at least one quality point as center of gravity on the basis of positions of the characteristic values in the polar coordinate system, wherein according to the invention, said quality point determining means in said data processing unit determine the at least one quality point as center of gravity of hypothetical masses assigned to the positions of the characteristic values in such a way that amounts of said masses correspond to the characteristic values to which they are assigned.

In a preferred embodiment of the apparatus said quality point determining means determine the at least one quality point as center of gravity of hypothetical mass points located at the positions of the characteristic values in such a way that amounts of said mass points correspond to the characteristic values to which they are assigned linearly or quadratically.

A further preferred embodiment of the apparatus according to the invention is characterised by the fact that said quality point determining means comprise means which, after determination of each characteristic value, calculate components of coordinates of a quality point, add these components to sums of the components calculated previously and define the coordinates of the quality point as values proportional to the sums obtained after the determination of the last characteristic value.

Another aspect of the invention relates to an apparatus for qualifying an object in two dimensions comprising a device for determining characteristic values of the object as function of a parameter for image points of a two-dimensional picture of the object and a data processing unit for qualifying the object on the basis of the characteristic values determined for each image point. According to the invention, said data processing unit comprises means for arranging the characteristic values for each image point in a sequence in a polar coordinate system having an origin, means for determining a quality point as center of gravity on the basis of positions of the characteristic values in the polar coordinate system for each image point, said means for determining, after determination of each characteristic value, calculating components of coordinates of the quality point for each image point, adding these components to sums of the components calculated previously and defining the coordinates of the quality point as values proportional to the sums obtained after the determination of the last characteristic value, and further comprises means for qualifying the object according to the position of the quality point determined in the polar coordinate system for each image point.

By this method the apparatus continuously generates appropriate values of the coordinates after the determination of each characteristic value, therefore, earlier values are not to be stored and at the end of the process the values of the coordinates are available immediately. In this way, even in the case of a large number of characteristic values, e.g. more than one thousand values, and a large number of image points, the end result can be obtained quickly with relatively low calculating capacity.

BRIEF DESCRIPTION OF DRAWINGS

The invention will hereinafter be described on the basis of drawings by demonstrating exemplary embodiments, where.

DISCUSSION OF THE PREFERRED EMBODIMENTS

Figure 1:
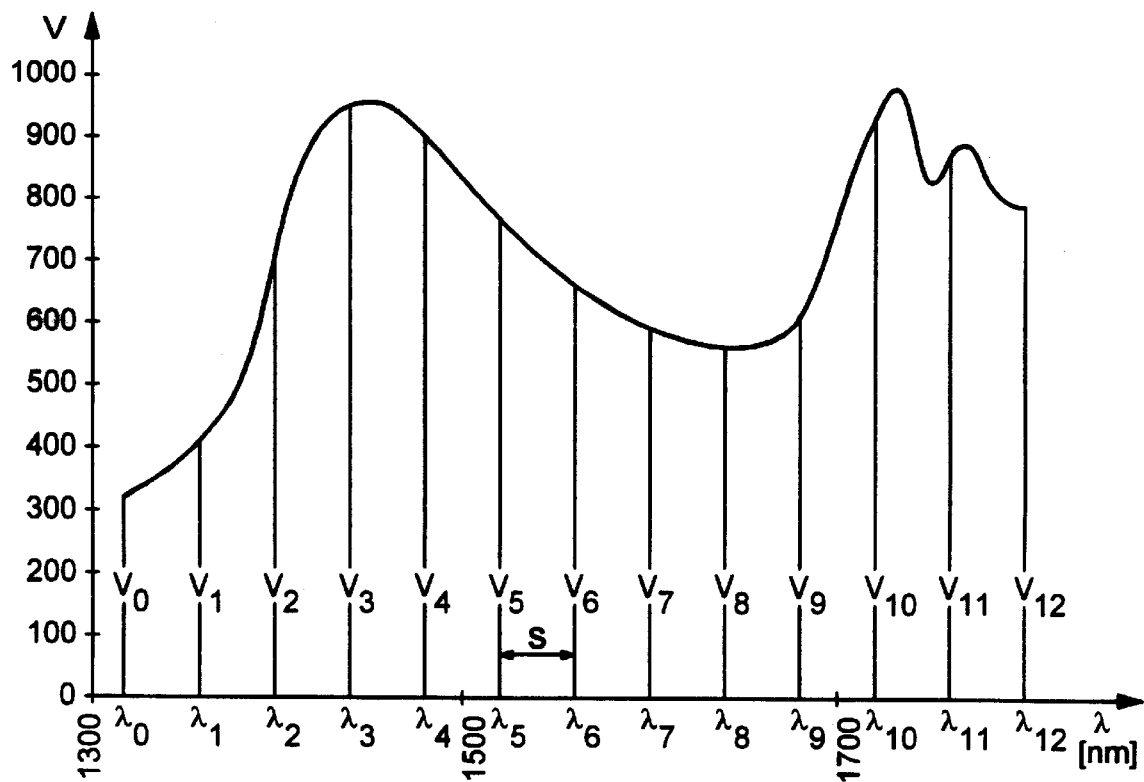
FIG. 1 is a reflection spectrum of an object recorded in the NIR range.

In the drawings, identical elements or elements of identical function are shown with the same reference signs.

FIG. 1 shows a reflection NIR spectrum of an examined object, in this case goose liver, in the wavelength range of 1320 to 1800 nm, in a rectangular coordinate system. Spectrum values of $V_0, V_1, \ldots V_i, \ldots V_{12}$ are associated with wavelength values of $\lambda_0, \lambda_1, \ldots \lambda_i, \ldots \lambda_{12}$, where i=0, 1, ... k, and so the number of the spectrum values is (k+1)=13.

Figure 2:
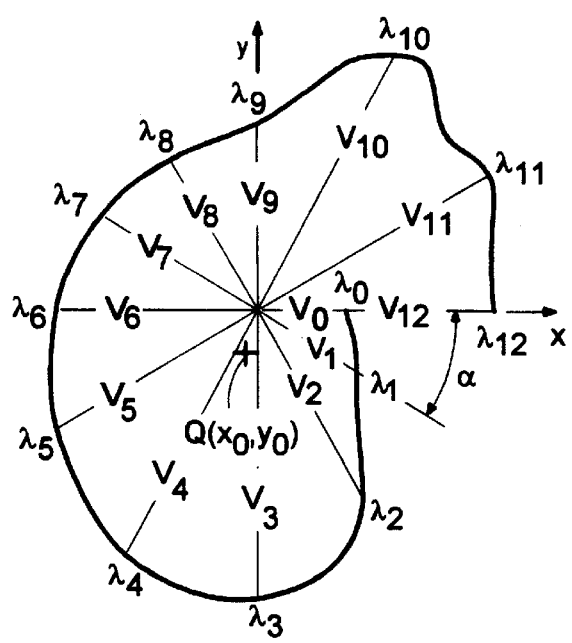
FIG. 2 is the spectrum as per FIG. 1 plotted in a polar coordinate system, FIG. 3 demonstrates one embodiment of the qualification method according to the invention, based on the spectrum in FIG. 2, FIG. 4 demonstrates another embodiment of the qualification method according to the invention, based on the spectrum in FIG. 2.

FIG. 2 shows the spectrum of FIG. 1 in a polar coordinate system, where spectrum values of $V_0, V_1, \ldots V_{12}$ are plotted as a function of angle $\alpha$. In the polar coordinate system an angular range of 0 to 360° corresponds to the wavelength range of 1320 to 1800 nm, and so the wavelength spacing of S=40 nm represents an angular increment of $\alpha$=30°. The plane of the polar coordinate system is called quality plane and in this plane a quality point Q is characterised by coordinates $x_0$ and $y_0$. A vector directed from the origin of the polar coordinate system to the quality point Q is called quality vector.

Quality point Q characterises the quality (composition) of the examined object, e.g. a material sample. For each object there is a corresponding quality point Q in the quality plane. However, the inverse of this statement is not true, because several objects of different qualities may result in the same quality point Q. Although the probability is extremely low that two different spectra have their quality points at the same point, this may happen in principle. In such a case, two quality planes may be used, for example by making an angular range of 2*360° correspond to the measured wavelength range. Then, the probability is practically zero that the quality points Q1 and Q2 determined from spectrum values measured in two different wavelength ranges for two objects of different qualities are at the same points.

Figure 3:
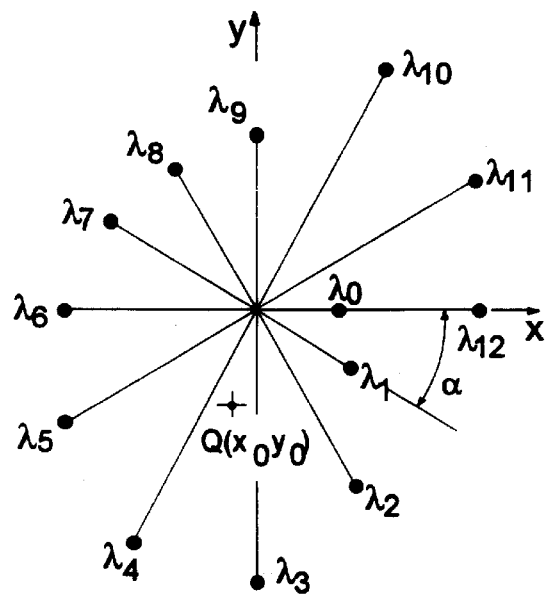
Figure 4:
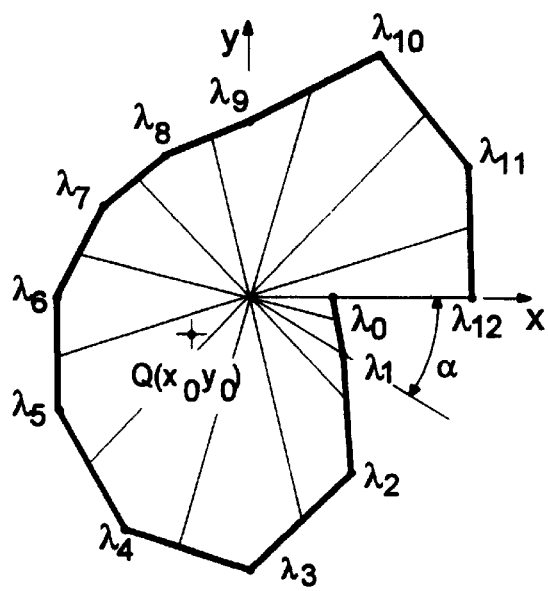
Figure 5:
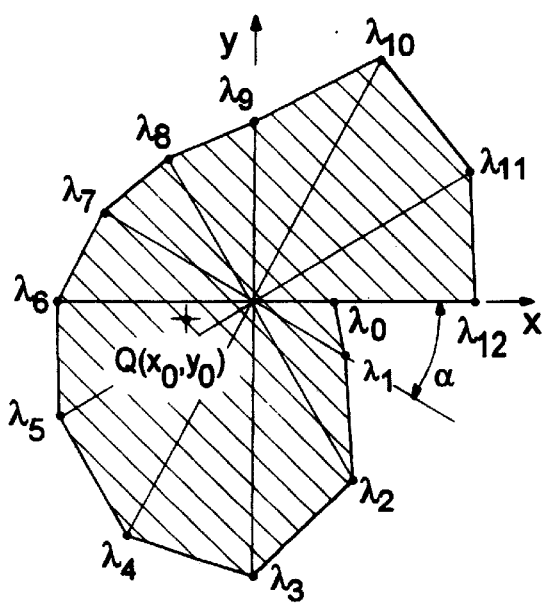
FIG. 5 is demonstrates a further embodiment of the qualification method according to the invention, based on the spectrum in FIG. 2.

The determination of the coordinates $x_0$ and $y_0$ of the quality point Q according to FIG. 2 is depicted in FIGS. 3, 4 and 5 on the basis of methods according to the invention. In all the three cases, the coordinates $x_0$ and $y_0$ of the quality point Q are determined from sums of linear series.

According to FIG. 3, for a spectrum plotted in the polar coordinate system, the method to be applied according to the invention is the following. Hypothetical mass points are assigned to the spectrum points corresponding to the obtained spectrum values, wherein the amounts of masses of the mass points linearly correspond to the spectrum values to which they are assigned, then the center of gravity of the mass points are determined, which center of gravity is considered as the quality point Q. The coordinates $x_0$ and $y_0$ of the quality point Q may be determined from the measured spectrum values on the basis of sums of the following linear series:

$$x_0 = \frac{1}{k+1}\sum_{i=0}^{k} x_i, \quad \text{where} \quad x_i = V_i^2 \cos i\alpha \tag{1}$$

$$y_0 = \frac{1}{k+1}\sum_{i=0}^{k} y_i, \quad \text{where} \quad y_i = V_i^2 \sin i\alpha \tag{2}$$

where $V_i$ is the spectrum value measured on the i-th wavelength value, k+1 is the number of the spectrum values, $\alpha[°]$=360/k. If the wavelength range is $(\lambda_{max}-\lambda_{min})$, the wavelength spacing used for recording the spectrum is $S=(\lambda_{max}-\lambda_{min})/k$. If hypothetical mass points of mass amounts corresponding quadratically to the respective spectrum values are assigned to the spectrum points corresponding to the spectrum values, $V_i^2$ has to be replaced by $V_i^3$ in equations (1) and (2).

FIG. 4 depicts another way of implementing the method according to the invention. In this case the center of gravity of straight lines connecting spectrum points corresponding to consecutive spectrum values and having masses corresponding to their lengths is considered to be the quality point Q. In this way, it can be achieved that absorption peaks characterising the composition play a more significant role in determining the quality point Q. This method practically means that the spectrum values are taken into account in a way weighted linearly with their distance from the origin. The coordinates $x_0$ and $y_0$ of the quality point Q can be determined from sums of the following linear series:

$$x_0 = \frac{1}{k}\sum_{i=1}^{k} x_i, \text{ where} \tag{3}$$

$$x_i = \sqrt{[V_i\cos i\alpha - V_{(i-1)}\cos(i-1)\alpha]^2 + [V_i\sin i\alpha - V_{(i-1)}\sin(i-1)\alpha]^2} * \frac{V_i\cos i\alpha - V_{(i-1)}\cos(i-1)\alpha}{2}$$

$$y_0 = \frac{1}{k}\sum_{i=1}^{k} y_i, \text{ where} \tag{4}$$

$$y_i = \sqrt{[V_i\cos i\alpha - V_{(i-1)}\cos(i-1)\alpha]^2 + [V_i\sin i\alpha - V_{(i-1)}\sin(i-1)\alpha]^2} * \frac{V_i\sin i\alpha - V_{(i-1)}\sin(i-1)\alpha}{2},$$

where the symbols correspond to those applied in equations (1) and (2).

FIG. 5 depicts another way of implementing the method according to the invention. In this case the center of gravity of surface portions confined by straight lines connecting spectrum points corresponding to consecutive spectrum values and the origin and having masses corresponding to their areas, that is the center of gravity of the surface area cut along the spectrum, is considered to be the quality point Q. This method practically means that spectrum values are taken into account in a way weighted quadratically with their distance from the origin. The coordinates $x_0$ and $y_0$ of the quality point Q can be determined from sums of the following linear series:

$$x_0 = \frac{1}{k}\sum_{i=1}^{k} x_i, \text{ where} \quad (5)$$

$$x_i = \frac{V_i V_{(i-1)}\sin\alpha}{2} * \frac{V_i\cos i\alpha + V_{(i-1)}\cos(i-1)\alpha}{3},$$

$$y_0 = \frac{1}{k}\sum_{i=1}^{k} y_i, \text{ where} \quad (6)$$

$$y_i = \frac{V_i V_{(i-1)}\sin\alpha}{2} * \frac{V_i\sin i\alpha + V_{(i-1)}\sin(i-1)\alpha}{3},$$

where the symbols correspond to those applied in equations (1) and (2).

It is to be noted that the methods according to FIGS. 3, 4 and 5 result in quality points Q of different positions, as it can be seen from equations (1)–(2), (3)–(4) and (5)–(6). In a particular qualification, of course, only one type of method shall be used.

Figure 6:
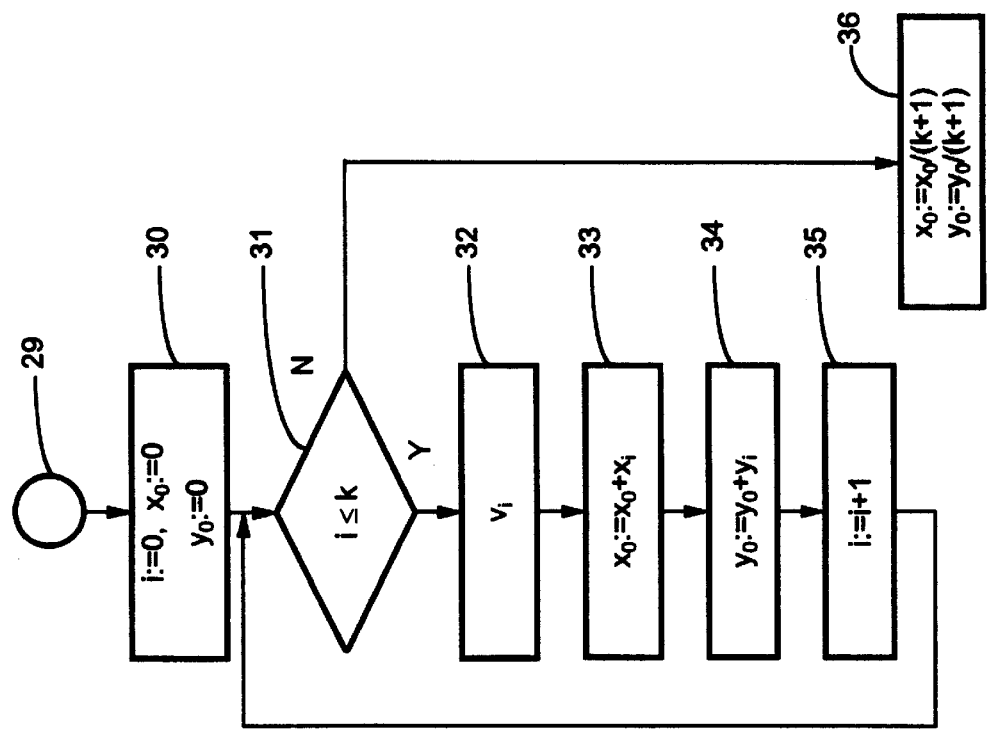
FIG. 6 is a flow diagram of an algorithm that can be applied in the method according to the invention depicted in FIG. 3.

In FIG. 6 the flow diagram shows a preferred calculation algorithm for generating the coordinate values $x_0$ and $y_0$ according to the equations (1) and (2). After step 21 (START), in step 30 an adjustment of index i and values of coordinates $x_0$ and $y_0$ to an initial zero takes place. In step 31 it is to be decided whether the value of i is lower than or equal to k, where k+1 is the number of the spectrum values. If the answer is yes (Y), measurement or determination of the spectrum value $V_i$ associated with index i takes place in step 32, then in step 33 value $x_i$ associated with the i-th spectrum value is calculated and this is added to the value of $x_i$ already determined, and in step 34 value $y_i$ associated with the i-th spectrum value is calculated and this is added to the value of $y_i$ already determined. Next, in step 35 the value of i is incremented, and then the program returns to step 31 and the cycle is repeated for the next spectrum value. If in step 31 the answer is no (N), that is i is greater than k, then all the spectrum values have been measured and considered, and so in step 36 the coordinate values $x_0=\Sigma x_i/(k+1)$ and $y_0=\Sigma y_i/(k+1)$ are calculated, and these values are stored or displayed, respectively, by a data processing unit.

Figure 7:
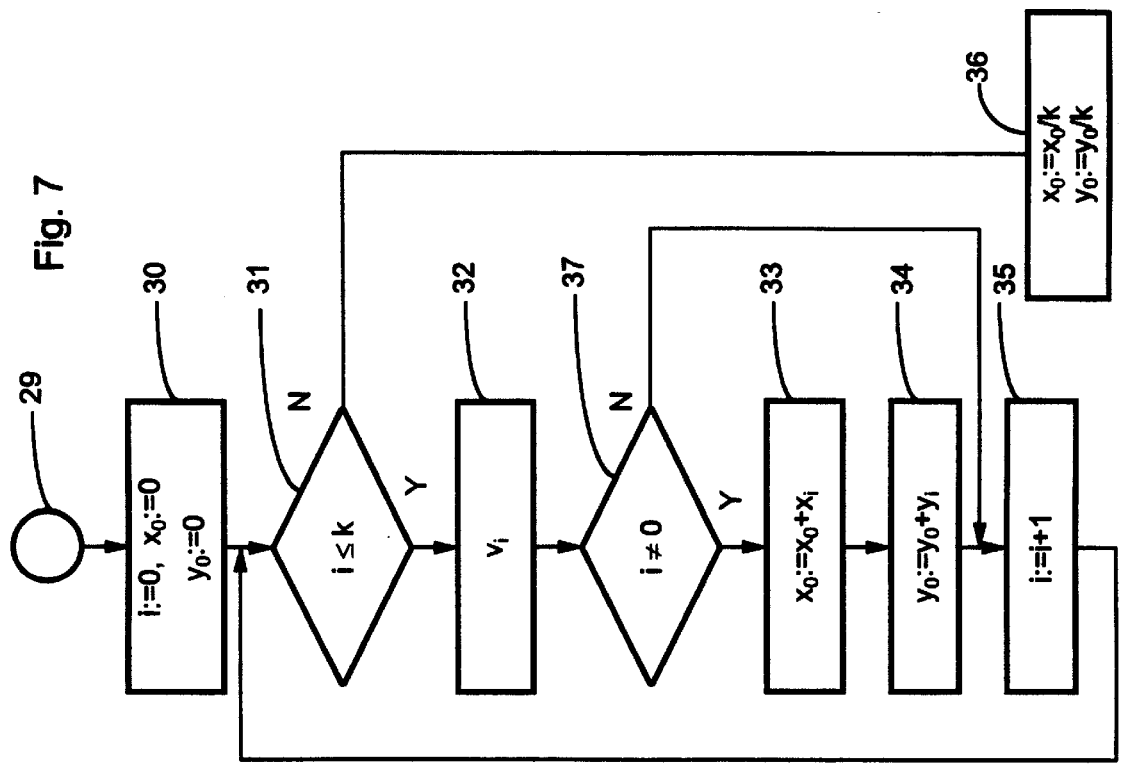
FIG. 7 is a flow diagram of an algorithm that can be applied in the method of the invention depicted in FIGS. 4 and 5.

In FIG. 7 the flow diagram shows a preferred calculation algorithm for generating the coordinate values $x_0$ and $y_0$ according to the equations (3) and (4), and (5) and (6), respectively. After step 29 (START), in step 30 an adjustment of index i and the values of coordinates $x_0$ and $y_0$ to an initial zero takes place. In step 31 it is to be decided whether the value of i is lower than or equal to k, where k+1 is the number of the spectrum values. If the answer is yes (Y), in step 32 measurement or determination of the spectrum value $V_i$ associated with index i takes place, then it is examined in step 37 whether the value of i is zero. If i=0, that is the very first spectrum value has been determined, no calculation takes place, but in step 35 the value of i is incremented. If i≠0, then in step 33 value $x_i$ associated with the i-th spectrum value is calculated and this is added to the value of $x_i$ already determined, and in step 34 value of $y_i$ associated with the i-th spectrum value is calculated and this is added to the value of $y_i$ already determined. Then in step 35 the value of i is incremented, and then the program returns to step 31 and the cycle is repeated for the next spectrum value. If in step 31 the answer is no (N), i.e. i is greater than k, then all the spectrum values have been measured and considered, and so in step 36 the coordinate values $x_0=\Sigma x_i/k$ and $y_0=\Sigma y_i/k$ are calculated, and these values are stored or displayed, respectively, by a data processing unit.

In the case when the method according to the invention is applied on the basis of such characteristics of the examined object that are already available and stored in the data processing unit, the step 32 is omitted in the flow diagrams depicted in FIGS. 6 and 7.

Figure 8:
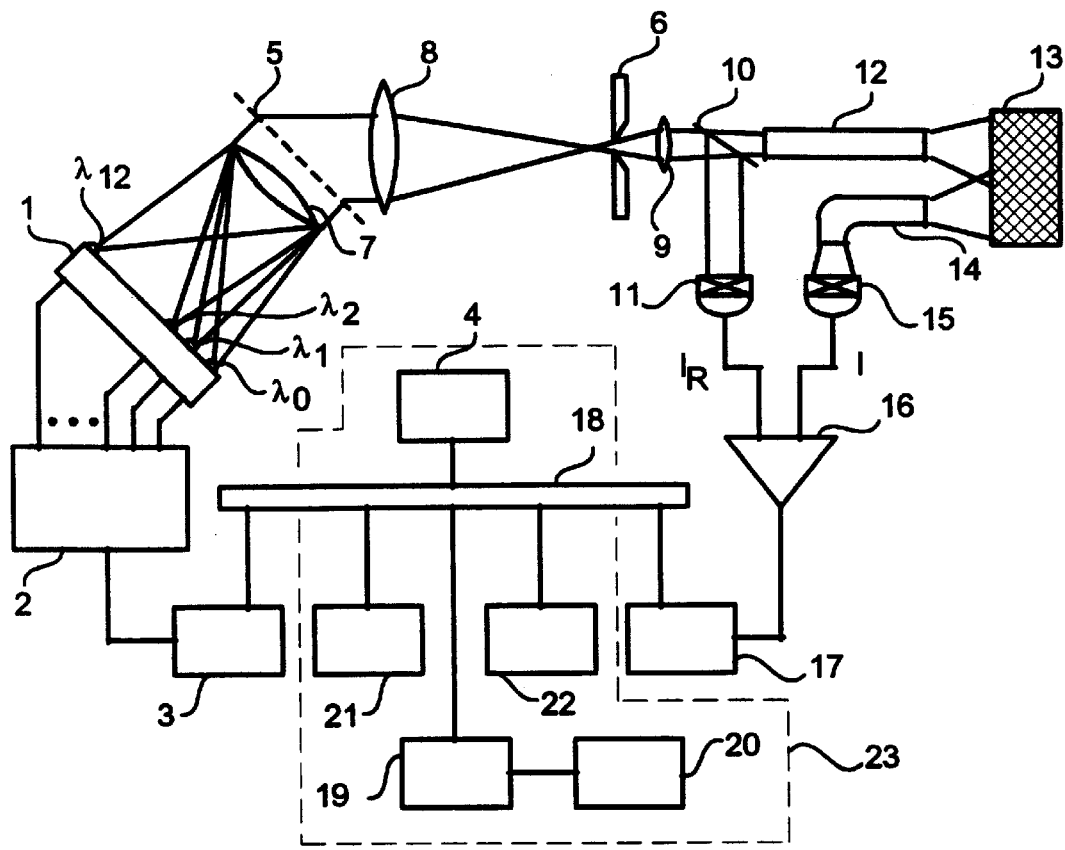
FIG. 8 is a schematic block diagram of an embodiment of the apparatus according to the invention.

In FIG. 8 the apparatus according to the invention is demonstrated by an example of a composition measurement instrument operating in the NIR wavelength range of electromagnetic radiation. The NIR wavelength range is especially suitable for determining rapidly and in a nondestructive way the concentration of components in a material and the composition of materials from the spectrum values, because in this range most organic materials have absorption bands, that is the spectrum has a rich information content. In addition, materials are the most transparent in this range, and so in the case of transmission or reflection measurements, as a result of larger sample thickness and deeper penetration, difficulties stemming from inhomogeneity can be eliminated.

The apparatus shown in FIG. 8 contains neither rotating nor moving elements, and would not require sampling and thus has a long lifetime. Radiation is ensured by a LED array 1 emitting cold light, the LEDs of which receive in turn actuating current pulses from a LED drive unit 2. The LED drive unit 2 is controlled through an I/O unit 3 by means of a microprocessor-based data processing unit 23 as described later. In the data processing unit 23, there is a CPU 4 to which a RAM 21, a ROM 22 and via I/O unit 19 a display 20 (monitor or LCD display) are connected through a bus 18. The I/O unit 3 and an A/D converter 17 are also connected to the bus 18. The spectral distribution and bandwidth of the radiation of the LEDs generally do not provide sufficient monochromatic radiation, and so an appropriately narrow bandwidth is provided by a transmission optical grating 5 and a slit 6. The monochromatic radiation of appropriately narrow bandwidth may also be ensured in a way different from that shown, e.g. by a reflection optical grating or by a monochromator of another type, e.g. by an opto-acoustic filter to be tuned by an electric control signal. A collimator lens 7 in front of the optical grating 5 and an imaging lens 8 after it perform the functions of collimation (paralleling) and imaging. The monochromatic radiation beam exiting from the slit 6 is paralleled by a lens 9, which parallel beam is divided into two by a beam splitter 10, preferably by a transparent glass plate positioned at an angle of 45°. The one smaller part reaches a reference detector 11, while the other larger part serves for illuminating the examined object 13, e.g. a material sample, through fibre optics 12. The radiation reflected by the object 13 or transmitting through it is guided by another fiber optics 14 to a measuring detector 15. Signal $I_R$ of the reference detector 11 and signal I of the measuring detector 15 are connected to inputs of a twin logarithmic amplifier 16, which provides at its output a signal proportional to the logarithm of the quotient $I/I_R$ of the signals. The output signal of the twin logarithmic amplifier 16 is supplied through the AND converter 17 to the CPU 4 for processing, which latter displays the result, e.g. the quality vector characterising the examined object 13, on the display 20. All this is performed in the following way.

After switch-on, at the command of the CPU 4 e.g. LED No. 0 in the LED array 1 consisting of thirteen LEDs receives a current pulse and its radiation reaches lens 7, which parallels the beam and supplies it to the optical grating 5, which emits a monochromatic radiation of wavelength $\lambda_0$ by means of the lens 8 through the slit 6. This monochromatic radiation partly reaches the reference detector 11 and partly through fiber optics 12 and 14 the object 13, and reflected by or transmitting through it, it reaches the measuring detector 15.

Figure 9:
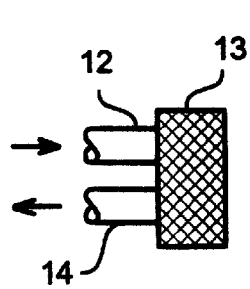
FIG. 9 is a schematic view illustrating a spectrum recording of the examined object based on interaction in the apparatus as per FIG. 8.
Figure 10:
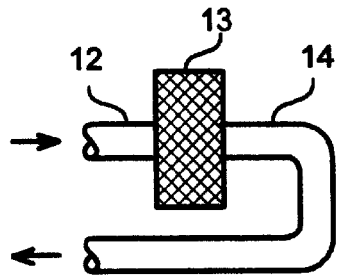
FIG. 10 is a schematic view illustrating a spectrum recording of the examined object based on transmittance in the apparatus as per FIG. 8.
Figure 11:
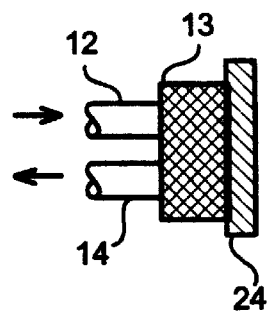
FIG. 11 is a schematic view illustrating a spectrum recording of the examined object based on transflectance in the apparatus as per FIG. 8.

The geometric arrangement between the object 13 and the fiber optics 12 and 14 may be different depending on what type of measurement is involved: reflectance shown in FIG. 8, interactance shown in FIG. 9, transmittance shown in FIG. 10 or, in the case of transparent liquids, for example by means of a reflecting surface 24 located behind a metering vessel (cuvette), transflectance shown in FIG. 11.

The logarithm of signals I and $I_R$ and the difference of the logarithms are generated by the twin logarithmic amplifier 16. Thus, according to equation $$\log I - \log I_R = \log(I/I_R)_{object, \lambda_0} \quad (7)$$

the logarithm of the quotient of the signals I and $I_R$ appears at the output of the twin logarithmic amplifier 16. In this way, the error resulting from alterations in the intensity of LED radiation may be eliminated. This signal is digitised by the A/D converter 17 and in the CPU 4 it is divided by a value of $\log(I/I_R)_{standard, \lambda_0}$ stored in the ROM 22 and obtained at the same wavelength $\lambda_0$ from a standard material (usually ceramic). The spectrum value $V_0$ so determined is associated with the wavelength $\lambda_0$. By generating the quotient of the signals appearing at the output of the twin logarithmic amplifier 16 and stemming from the object 13 and from the standard material, any error resulting from alterations in time of the reference detector 11 and the measuring detector 15 may be eliminated. Since the characteristics of the reference detector 11 and the measuring detector 15 change slowly, it is sufficient to re-measure and store the spectrum values of the standard material at longer intervals, e.g. in every month.

After that the CPU 4, e.g. according to the flow diagram shown in FIG. 6, calculates values of the first members of the series according to the formulae specified for $x_i$ and $y_i$ relating to $\lambda_0$. This was the first cycle.

In the next cycle, at the command of the CPU 4, LED No. 1 receives a pulse and as a result, in the way described above, a monochromatic radiation of wavelength $\lambda_1$ appears at the slit 6, which radiation proceeds across the two channels in the way described above. By dividing the value of $\log(I/I_R)_{object, \lambda_1}$ appearing at the output of the twin logarithmic amplifier 16 by a value of $\log(I/I_R)_{standard, \lambda_i}$ measured on the standard material, spectrum value $V_1$ associated with wavelength $\lambda_1$ is determined. The CPU 4 calculates values of the second members of the series according to the formulae specified for $x_i$ and $y_i$ relating to $\lambda_1$, which are added to the values calculated in the previous cycle.

The process continues like this until the last LED No. 12 in this example is actuated, until the last members of series $x_i$ and $y_i$ relating to $\lambda_{12}$ and then the complete sums of the series are calculated, along with the coordinate values $x_0$ and $y_0$ of the quality point Q, and until these are displayed by the display 20. Of course at the display 20 quality point Q of a reference product may also be displayed simultaneously, and in fact data of a distance $D_{polar}$ to be described below may also be indicated. In the example above, there were thirteen spectrum values, but it may also be several hundred or several thousand, the method is the same but it is repeated several times.

Figure 12:
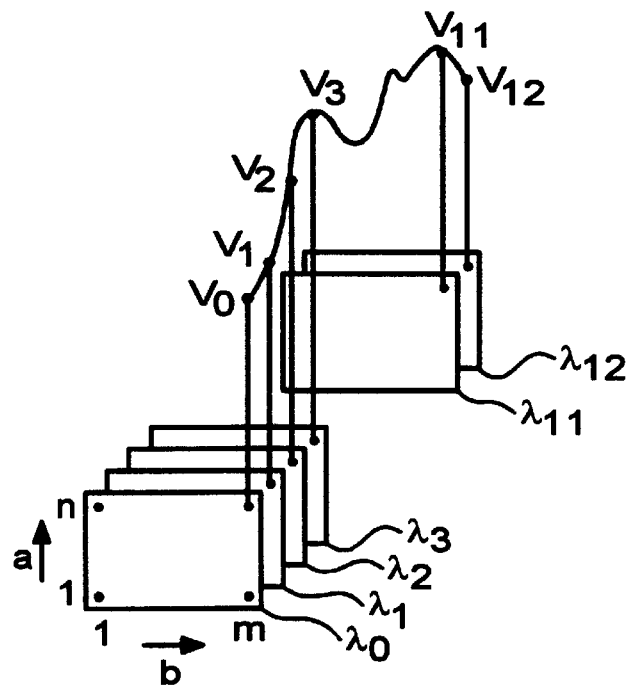
FIG. 12 is a schematic diagram depicting spectrum recording in two dimensions.

FIG. 12 illustrates spectrum recording of an object taken in two dimensions at several wavelength values. The two-dimensional picture of the object, the image field are divided into image points, and each image point may be characterised by image point coordinates a and b. The value of image point coordinate a ranges from 1 to n, and the value of image point coordinate b ranges from 1 to m, that is the image field consists of n lines, m columns and n*m image points.

As a result of the two-dimensional spectrum recording, at each $\lambda_i$ wavelength value, n*m spectrum values $V_i(a, b)$ will be obtained, where i=0, 1 ... k. Thus, a complete spectrum will be associated with each image point. In the example shown in FIG. 12, wavelength value $\lambda_0, \lambda_1, \ldots \lambda_{12}$ are associated with spectrum values $V_0, V_1, \ldots V_{12}$ at image point a=n, b=m. In a real case, the number of image points may be higher than 100,000 and the number of wavelength values applied could exceed 1000. Therefore, the number of spectrum values could be higher than 100 million, and each spectrum value represents a data of at least 8 bits.

According to the invention, each image point of the image field is characterised by a quality point determined on the basis of the spectrum, and the position of the quality point is specified by two coordinates. Various possibilities for determining the quality point are described in relation to FIGS. 1 to 5.

Figure 13:
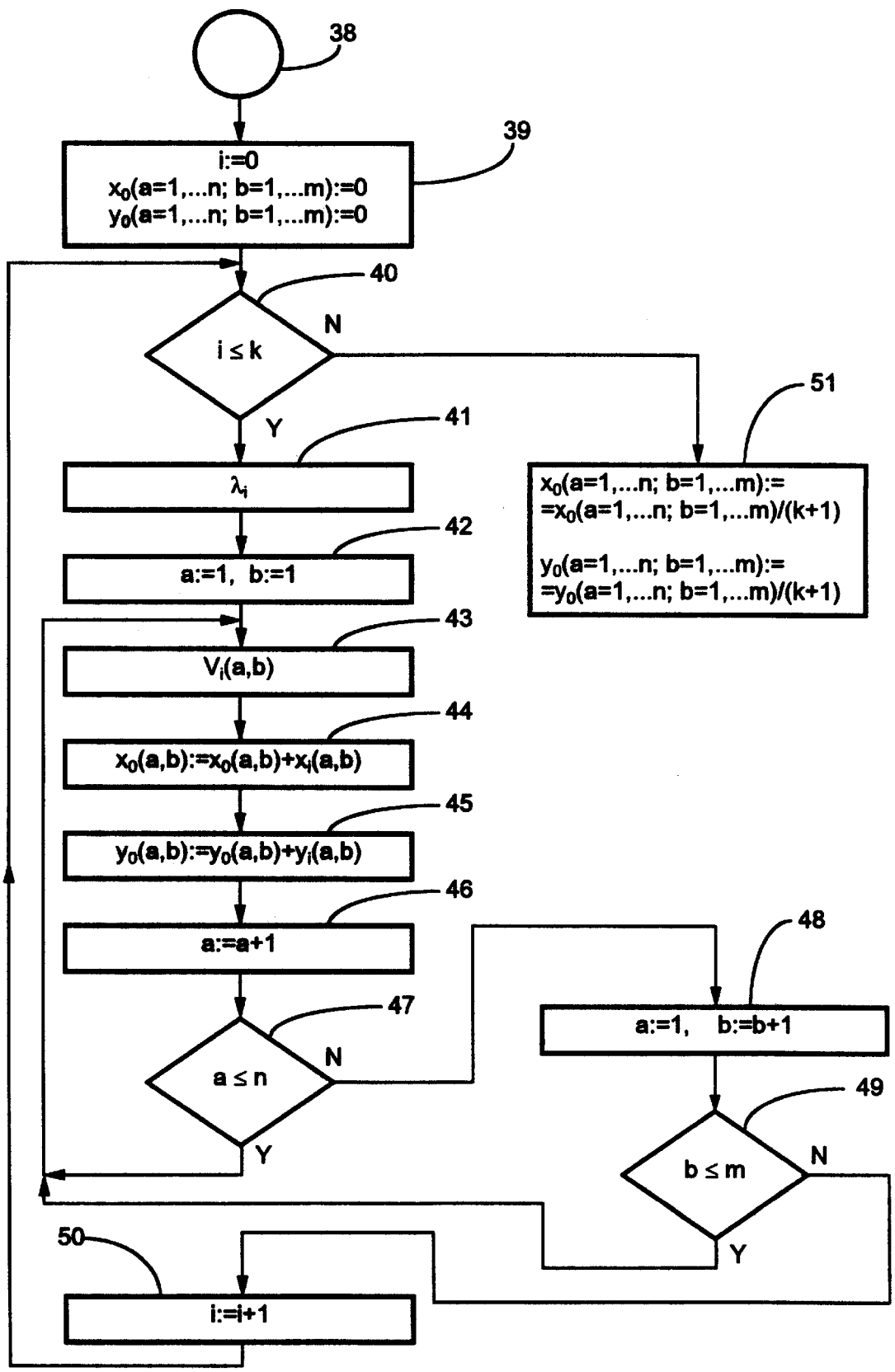
FIG. 13 is a flow diagram of an algorithm that can be applied in the method of the invention as depicted in FIG. 3.

In FIG. 13 the flow diagram shows a preferred calculation algorithm for generating the coordinate values $x_0$ and $y_0$ for each image point, according to the equations (1) and (2). For the coordinates of the image points, the symbols of FIG. 12 are used. After step 38 (START), in step 39 an adjustment of index i and values of coordinates $x_0$ and $y_0$ for all image points to an initial zero takes place. In step 40 it is to be decided whether the value of i is lower than or equal to k, where k+1 is the number of the spectrum values. If the answer is yes (Y), in step 41 the adjustment of wavelength value $\lambda_i$ associated with index i takes place, and then the spectrum values are measured and determined, respectively, for each image point. For this, in step 42 the image point coordinates a and b are set to an initial value 1, and in step 43 the measurement and determination, respectively, of spectrum value $V_i(a, b)$ associated with the specified image point take place, then in step 44 value $x_i(a, b)$ associated with this spectrum value is calculated, and this is added to the value of $x_i(a, b)$ already determined, and in step 45 the value $y_i(a, b)$ associated with the spectrum value is calculated and added to the value of $y_i(a, b)$ already determined. Next, in step 46 image point coordinate a is incremented and it is examined in step 47 whether the value of a is lower than or equal to n, where n is the number of the lines of the image field. If yes (Y), the program returns to step 43 and the cycle is repeated for the next image points. If no (N), then all the image points in the first column of the image field have been measured and taken into consideration, so the program changes to the next column. For this, the image point coordinate b is incremented in step 48 and the image point coordinate a is again set to the value 1. Then in step 49 it is examined whether the value of b is lower than or equal to m, where m is the number of the columns in the image field. If yes (Y), the program returns to step 43 and the cycle is repeated for the image points of the next column. If no (N), all the image points of all columns in the image field have been measured and taken into consideration, so in step 50 the value of i is incremented and then the program returns to step 40 and the complete cycle is repeated for the next wavelength value. If in step 40 the response is no (N), that is i is greater than k, all the spectrum values have been measured and taken into consideration for all the image points, and so in step 51 the coordinate values $x_0$ (a, b)=$\Sigma x_i(a, b)/(k+1)$ and $y_0(a, b) = \Sigma y_i(a, b)/(k+1)$ are calculated for all image points, and these values are stored or displayed, respectively, by the data processing unit.

Figure 14:
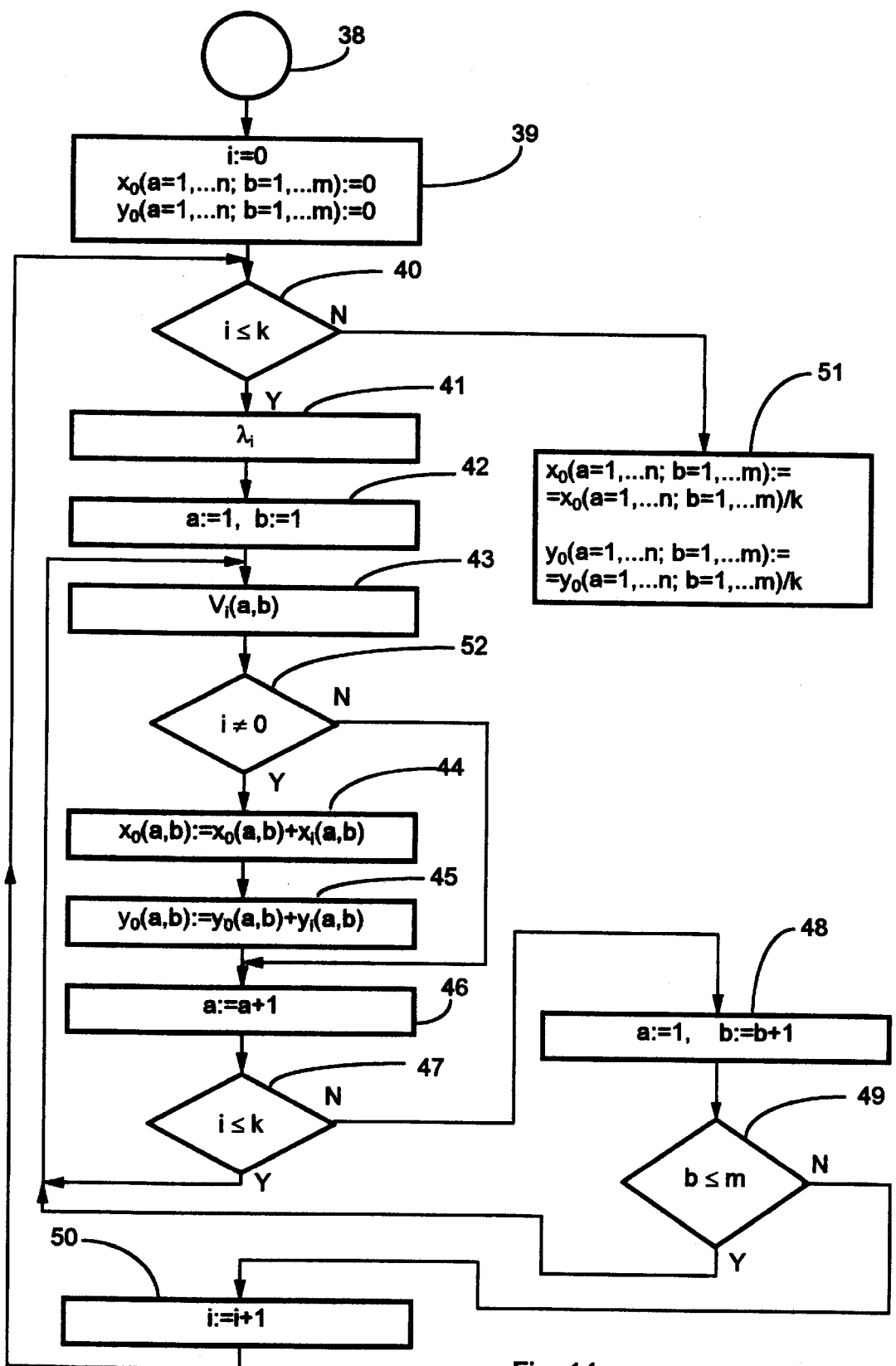
FIG. 14 is a flow diagram of an algorithm that can be applied in the method of the invention as depicted in FIGS. 4 and 5.

In FIG. 14 the flow diagram shows a preferred calculation algorithms for generating coordinate values $x_0$ and $y_0$ for each image point, according to the equations (3) and (4), and (5) and (6), respectively. The flow diagram shown in FIG. 14 is similar to that depicted in FIG. 13, therefore, only the differing parts will be described. After step 43 it is examined in step 52, whether the value of i is zero. If i=0, that is the spectrum value associated with the very first wavelength value $\lambda_0$ has been determined, no calculation is carried out in steps 44 and 45, but the program continues in step 46 with the incrementing of value a. The other deviation from the algorithm shown in FIG. 13 is that in step 51 the coordinate values are calculated according to the equations $x_0(a, b)=\Sigma x_i (a, b)/k$ and $y_0(a, b)=\Sigma y_i(a, b)/k$.

In the case when the method according to the invention is applied on the basis of such characteristics of the examined object that are already available and stored in the data processing unit, the steps 41 and 43 in the flow diagrams according to FIGS. 13 and 14 are omitted.

Figure 15:
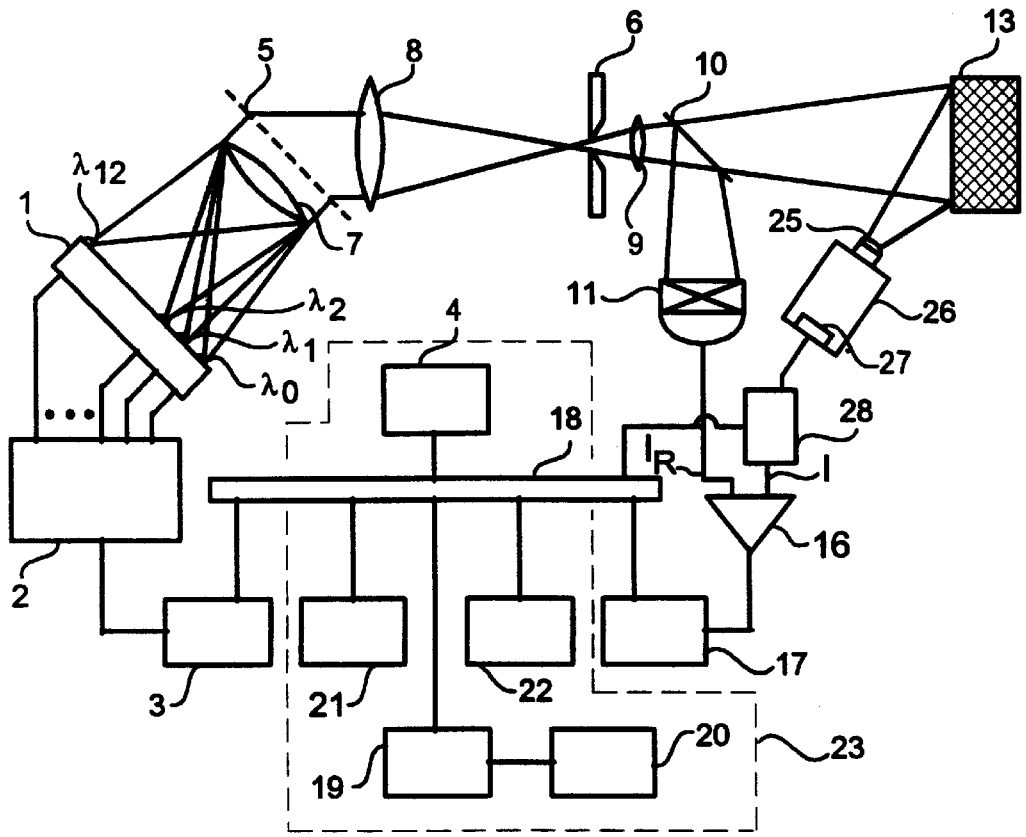
FIG. 15 is a schematic block diagram of an embodiment of the apparatus according to the invention.

FIG. 15 shows an apparatus according to the invention by way of example of a two-dimensional composition measurement instrument functioning in the NIR wavelength range of electromagnetic radiation. The apparatus contains neither rotating nor moving elements, and does not require sampling and thus has a long lifetime. Radiation is ensured by a LED array 1 emitting cold light, the LEDs of which receive in turn actuating current pulses from a LED drive unit 2. The LED drive unit 2 is controlled through an I/O unit 3 by means of a microprocessor-based data processing unit 23 as described later. In the data processing unit 23, there is a CPU 4 to which a RAM 21, a ROM 22 and via I/O unit 19 a display 20 (monitor or LCD display) are connected through a bus 18. The I/O unit 3, a multiplexer 28 and an A/D converter 17 are also connected to the bus 18. The spectral distribution and bandwidth of the radiation of the LEDs generally do not provide sufficient monochromatic radiation, and so an appropriately narrow bandwidth is provided by a transmission optical grating 5 and a slit 6. The monochromatic radiation of appropriately narrow bandwidth may also be ensured in any per se known way different from that shown. A collimator lens 7 in front of the optical grating 5 and an imaging lens 8 after it perform the functions of collimation (paralleling) and imaging. The monochromatic radiation beam exiting from the slit 6 is directed to a two-dimensional surface of the examined object 13 by a lens 9, which beam is divided into two by a beam splitter 10, preferably by a transparent glass plate positioned at an angle of 45°. The one smaller part reaches a reference detector 11, while the other larger part serves for illuminating the examined object 13, e.g. a material sample. The two-dimensional picture of the object 13 illuminated uniformly is imaged by a lens 25 to the surface of a photosensitive matrix 27 in a video camera 26. The photosensitive matrix 27, e.g. a CCD sensor, forms a photosensitive matrix of m columns and n lines, and each pixel of this matrix senses the intensity of the radiation reflected by one image point of the surface of the object 13, which intensity is characteristic of the material quality of that surface element of the object 13. The signals from the pixels are forwarded one by one in time by the multiplexer 28 to a twin logarithmic amplifier 16. The multiplexer 28 could be integrated in a single chip with the photosensitive matrix 27 of the CCD type. Signal $I_R$ of the reference detector 11 and signal I of the pixels of the photosensitive matrix 27 are connected to inputs of the twin logarithmic amplifier 16, which provides at its output a signal proportional to the logarithm of the quotient $I/I_R$ of the signals. The output signal of the twin logarithmic amplifier 16 is supplied through the AND converter 17 to the CPU 4 for processing, which latter displays the result, e.g. a two-dimensional distribution of a characteristic of the examined object 13, on the display 20. All this is performed in the following way.

After switch-on, at the command of the CPU 4 e.g. LED No. 0 in the LED array 1 consisting of 13 LEDs receives a current pulse and its radiation reaches lens 7, which parallels the beam and supplies it to the optical grating 5, which emits a monochromatic radiation of wavelength $\lambda_0$ by means of the lens 8 through the slit 6. This monochromatic radiation partly reaches the reference detector 11 and partly the object 13 as described above. Reflected by the object 13, the radiation reaches the photosensitive matrix 27, the pixels of which are regularly scanned by the multiplexer 28 at the command of the CPU 4. The logarithm of signals I and $I_R$ and the difference of logarithms are generated by the twin logarithmic amplifier 16. Thus, the logarithm of the quotient of the signals appears at the output of the twin logarithmic amplifier 16. In this way, the error resulting from alterations in the intensity of LED radiation may be eliminated. This signal is digitised by the AND converter 17 and divided by in the CPU 4 by a $\log(I/I_R)_{standard, \lambda_0}$ value stored in the ROM 22 and obtained at the same wavelength $\lambda_0$ from a standard material (usually ceramic). The spectrum values $V_0(a, b)$ so obtained are associated with the wavelength $\lambda_0$.

The CPU 4, e.g. according to the flow diagram shown in FIG. 13, after determining the spectrum value $V_0(a, b)$ corresponding to each image point, calculates values of the first members of the series of the formulae specified for $x_i$ and $y_i$ relating to $\lambda_0$. This was the first cycle and the following cycles relating to $\lambda_1, \lambda_2, \ldots$ are carried out likewise.

The process continues like this until the last LED No. 12 in this example is actuated, until the last members of $x_i$ and $y_i$ series relating to $\lambda_{12}$ and then the complete sums of the series are calculated, along with the coordinate values $x_0(a, b)$ and $y_0(a, b)$ of the quality point $Q(a, b)$, and until corresponding data or diagrams are displayed by the display 20. In the example above, there were thirteen spectrum values, but it may also be several hundred or several thousand, the method is the same but it is repeated several times.

The apparatus according to the invention may also be implemented in a way that the image of the object 13 is sensed through a changeable filter, which filter may be located in front of or may be integrated with the video camera 26. In this case, the object 13 is to be illuminated by a wide-band light beam including the required sensing wavelength values, or such wavelength values shall be used for the detection which correspond to the light illuminating the object 13.

Figure 16:
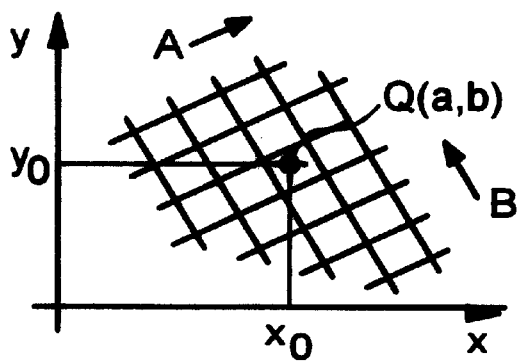
FIG. 16 is a schematic diagram illustrating the determination of qualities of an examined object on the basis of the quality point according to the invention.

FIG. 16 shows by way of example a quality plane, in which level lines associated with different values of two qualities of an object are plotted. For example component A could be starch and component B protein in qualifying a food industry object. From coordinates $x_0$ and $y_0$ of the quality point $Q(a, b)$ associated with a specific image point, the concentration of starch and protein in the image point can be determined.

Figure 17:
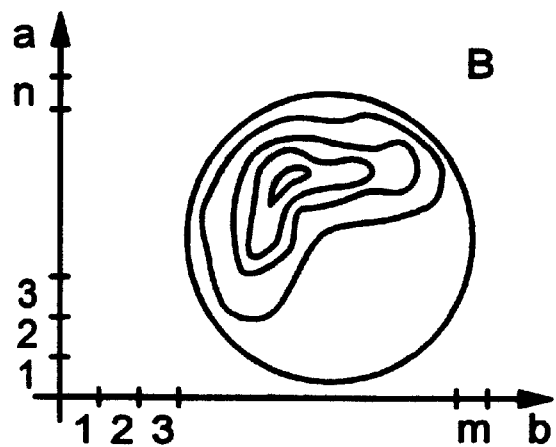
FIG. 17 is a two-dimensional distribution image of a quality of an examined object, generated by the method according to the invention.
Figure 18:
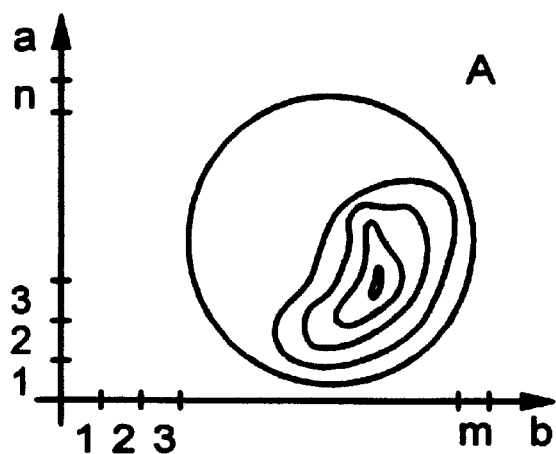
FIG. 18 is a two-dimensional distribution image of another quality of the examined object as per FIG. 17, generated by the method according to the invention.

FIGS. 17 and 18 depict diagrams that show two-dimensional distributions of quality values determined for each image point by means of the method illustrated in FIG. 16. FIG. 17 shows the distribution of component B, e.g. protein, and FIG. 18 depicts the distribution of component A, e.g. starch, in the case of a chicken leg put on a plate with potato garnish.

In the course of testing the method according to the invention in the practice we have come to the following insights. For production plant experts the method according to the present invention resulting in a substantial reduction of data can be easily applied because of its straightforward nature and simple interpretation. This is because in production processes in many cases it is not required to know exactly all the composition data (concentration values) characterizing a product, it is enough to know whether the product deviates from the quality of a reference product (a sample declared to be satisfactory) by an extent exceeding a predetermined rate or not. In such a case the extent of deviation may be described by a "distance" between the quality point of the reference product and that of the examined product. The distance may be defined as $$D_{polar} = \sqrt{(x_{0ref} - x_{0test})^2 + (y_{0ref} - y_{0test})^2} \qquad (8)$$

where $x_{0ref}$ and $y_{0ref}$ are coordinates of the quality point $Q_{ref}$ of the reference product, and $x_{0test}$ and $y_{0test}$ are those of the quality point Q of the examined product.

Consequently, around the quality point $Q_{ref}$ of the reference product a circle can be defined so that if the quality point Q is within the circle, the examined product may be accepted and if quality point Q is outside this circle, it is to be rejected. The method may be used either for classification or sorting.

Concerning the extent of deviations between spectra, distances have been defined in the prior art. Such distances are for example the Euclidean distance and the Mahalanobis distance. These distances specify the deviations well but say nothing about the reason of the difference and so two examined products being at an identical distance from a reference sample could differ very much from each other. On the contrary, in the quality plane according to the present invention conclusions can be drawn about the reason of deviation from the position of the quality point of the examined product. If for example, the quality point of examined goose liver deviates from the quality point of the reference goose liver in the same direction where the fat's absorption peak points in the polar coordinate system, this indicates that the fat content of the examined goose liver is higher than that of the reference goose liver. To this end, the wavelength range corresponding to 360° must be selected in a way that the directions of the absorption peaks of the two most important components make an angle of approximately 90° or 270° to each other in the polar coordinate system.

It is great advantage of the method according to the invention that it is not sensitive to the noise in the spectrum. The plus and minus deviations of high frequency noises offset one another in determining the position of the quality point Q, consequently it is not necessary to "smooth" the spectra. The method is neither sensitive to changes in particle size of the examined object nor to those in thickness in a transmission measurement. These changes affect the spectrum plotted in the polar coordinate system as if it were magnified or reduced in size, while the center of gravity remains in place.

The method does not require any learning process or calibration, and for qualifying a product it is only necessary to be aware of the reference product's spectrum. The method may be carried out extremely rapidly because by calculating the values of the members of the series serving for calculating the coordinates of the quality point Q for each wavelength, and by adding these values to the previous values, only the sums are carried forward and the values of the previous members in the series can be forgotten, and so by measuring the values associated with the last wavelength, only the last values are to be added for obtaining the result.

The method according to the invention, which is principally qualitative, may be further developed to make it quantitative. This is possible in two ways.

According to one method, in an empirical way, lines of levels concerning a specified quality of the object, e.g. equi-concentration lines relating to the concentration of a component, are to be determined in the quality plane. In determining the lines associated with different values of the specified quality, it is advisable to select the angular range corresponding to the value range in a way that it corresponds to a value range in which the relevant quality has specific effects. In consideration of this point, it could be advisable to apply several quality planes and accordingly several quality points for a quantitative determination of several qualities of the object.

According to another method, a specified quality, e.g. concentration K of a component, may be calculated in a predetermined concentration range with the following formula:

$$K = A + Bx_0 + Cy_0, \qquad (9)$$

where $x_0$ and $y_0$ are the coordinates of the quality point Q, and coefficients A, B and C may be determined by regression calculation.

The method according to the invention may be applied to any type of spectrum (optical, mechanical, electrical etc.) and to any of its transformed versions, or to any set of characteristics of an object which characteristics can be expressed in numbers and arranged in a sequence in a polar coordinate system.

We claim:

1. A method for qualifying an object, comprising the steps of:

determining several characteristic values of the object, at least two values being different from each other;

arranging the characteristic values in a sequence in a polar coordinate system having an origin;

assigning hypothetical masses to positions of the characteristic values, said masses being weighted as a function of the distance from an origin of said polar coordinate system;

determining at least one quality point as a center of gravity on the basis of the weighted characteristic values in the polar coordinate system; and qualifying the object according to a position of the at least one quality point;

wherein values of at least one quality of the object are determined from coordinate values of the at least one quality point according to a linear equation, wherein constants of the equation are obtained by regression calculation.

2. The method as claimed in claim 1, wherein said hypothetical masses assigned to the positions of the characteristic values are points located at the positions of the characteristic values, and wherein the values of masses of said points correspond to the characteristic values to which they are assigned linearly or quadratically.

3. The method as claimed in claim 1, wherein said hypothetical masses assigned to the positions of the characteristic values are straight lines connecting consecutive positions of the characteristic values, and wherein the values of masses of said lines correspond to their lengths.

4. The method as claimed in claim 1, wherein said hypothetical masses assigned to the positions of the characteristic values are surface portions confined by straight lines connecting consecutive positions of the characteristic values and the origin, and wherein the values of masses of said surface portions correspond to their areas.

5. The method as claimed in claim 1, wherein the object is qualified according to whether the quality point or any of the quality points falls into a predetermined domain defined in the polar coordinate system.

6. The method as claimed in claim 1, wherein the object is qualified according to whether the quality point or any of the quality points falls into any of two or more predetermined domains defined in the polar coordinate system.

7. The method as claimed in claim 1, wherein the object is qualified according to a distance between the quality point or any of the quality points and a reference quality point corresponding to a reference object.

8. The method as claimed in claim 1, wherein said several characteristic values of the object are determined as a function of a parameter, and the characteristic values are arranged in a sequence according to corresponding values of the parameter.

9. The method as claimed in claim 8, wherein said arranging the characteristic values in a sequence is carried out so that a whole value range of the parameter corresponds to an angular range of 360°, and particular value ranges of the parameter carrying specific information about qualities of the object make an angle of approximately 90° or 270° to each other in the polar coordinate system.

10. The method as claimed in claim 8, wherein said arranging the characteristic values in a sequence is carried out so that a whole value range of the parameter corresponds to two or more angular ranges in the polar coordinate system, a quality point is determined for each angular range, and the qualification of the object is carried out according to the two or more quality points.

11. A method for qualifying an object in two dimensions, comprising the steps of:
   determining several characteristic values of the object as a function of a parameter for each image point of a two dimensional picture of the object;
   arranging the characteristic values for each image point in a sequence in a polar coordinate system having an origin;
   determining a quality point as a center of gravity on the basis of positions of the characteristic values in the polar coordinate system for each image point by calculating components of coordinates of the quality point for each image point and adding these components to sums of the components calculated previously so that coordinates of the quality point are defined as values proportional to the sums obtained after the determination of the last characteristic value; and
   qualifying the object according to the position of the quality point determined in the polar coordinate system for each image point;
   wherein said values of the quality of the object are determined from the coordinate values of the quality point by a linear equation, wherein constants of the equation are obtained by regression calculation.

12. The method as claimed in claim 11, wherein a single quality point is determined for each image point and by averaging coordinates of the quality points obtained for the image points an average quality point is determined for the qualification of the object.

13. The method as claimed in claim 12, wherein a statistical parameter of distances between the quality points of the image points and the average quality point is determined and the object is qualified according to this statistical parameter.

14. The method as claimed in claim 12, wherein the object is qualified according to whether the quality points are within a predetermined distance from the average quality point.

15. The method as claimed in claim 11, wherein, on the basis of the quality point obtained for each image point, a value of a quality of the object is determined for each image point, and the object is qualified according to whether these values for the image points are within a predetermined value range.

16. The method as claimed in claim 11, wherein, on the basis of the quality point obtained for each image point, a value of a quality of the object is determined for each image point, then an average value is determined for all image points, and the object is qualified according to whether these values for the image points are within a predetermined range in relation to the average value.

17. The method as claimed in claim 11, wherein, on the basis of the quality point obtained for each image point, a value of a quality of the object is determined for each image point, and a two-dimensional distribution of the quality is generated.

18. The method as claimed in claim 11, wherein the quality point is determined as center of gravity of hypothetical masses assigned to the positions of the characteristic values in such a way that values of said masses correspond to the characteristic values to which they are assigned.

19. The method as claimed in claim 18, wherein said hypothetical masses assigned to the positions of the characteristic values are points located at the positions of the characteristic values, and wherein the values of masses of said points correspond to the characteristic values to which they are assigned linearly or quadratically.

20. An apparatus for qualifying an object, comprising:
   a device for determining several characteristic values of the object, at least two values being different from each other; and
   a data processing unit for arranging the characteristic values determined in a sequence in a polar coordinate system having an origin and for assigning hypothetical masses to positions of the characteristic values, said masses being weighted as a function of the distance from an origin of said polar coordinate system;
   said data processing unit including means for determining at least one quality point as a center of gravity on the basis of the weighted characteristic values in the polar coordinate system;
   wherein values of at least one quality of the object are determined from coordinate values of the at least one quality point according to a linear equation, wherein constants of the equation are obtained by regression calculation.

21. The apparatus as claimed in claim 20, wherein said quality point determining means determine the at least one quality point as center of gravity of hypothetical mass points located at the positions of the characteristic values in such a way that values of said mass points correspond to the characteristic values to which they are assigned linearly or quadratically.

22. The apparatus as claimed in claim 20, wherein said quality point determining means comprise means which, after determination of each characteristic value, calculate components of coordinates of a quality point, add these components to sums of the components calculated previously and define the coordinates of the quality point as values proportional to the sums obtained after the determination of the last characteristic value.

23. An apparatus for qualifying an object in two dimensions, comprising:
   a device for determining characteristic values of the object as a function of a parameter for image points of a two-dimensional picture of the object; and a data processing unit for qualifying the object on the basis of the characteristic values determined for each image point;

said data processing unit including means for arranging the characteristic values for each image point in a sequence in a polar coordinate system having an origin, means for determining a quality point as a center of gravity on the basis of positions of the characteristic values in the polar coordinate system for each image point and means for qualifying the object according to the position of the quality point determined for each image point;

wherein said means for determining calculates components of coordinates of the quality point for each image point, adds these components to sums of the components calculated previously and defines the coordinates of the quality point as values proportional to the sums obtained after the determination of the last characteristic value;

wherein said values of the quality of the object are determined from the coordinate values of the quality point by a linear equation, wherein constants of the equation are obtained by regression calculation.

24. The apparatus as claimed in claim 23, wherein said quality point determining means determine the quality point as center of gravity of hypothetical masses assigned to the positions of the characteristic values in such a way that values of said masses correspond to the characteristic values to which they are assigned.

25. The apparatus as claimed in claim 24, wherein said quality point determining means determine the quality point as center of gravity of hypothetical mass points located at the positions of the characteristic values in such a way that values of said mass points correspond to the characteristic values to which they are assigned linearly or quadratically.

* * * * *